United States Patent [19]

Kleinstück et al.

[11] 4,118,435
[45] Oct. 3, 1978

[54] CATALYZED PRODUCTION OF PHOSPHOROUS AND PHOSPHONOUS ACID ESTER CHLORIDES

[75] Inventors: Roland Kleinstück; Hans-Dieter Block, both of Cologne, Germany

[73] Assignee: Bayer Aktiengesellschaft, Leverkusen, Germany

[21] Appl. No.: 819,535

[22] Filed: Jul. 27, 1977

[30] Foreign Application Priority Data

Aug. 12, 1976 [DE] Fed. Rep. of Germany ....... 2636270

[51] Int. Cl.$^2$ ............................................. C07F 9/146
[52] U.S. Cl. .................................... 260/972; 260/960
[58] Field of Search ........................................ 260/972

[56] References Cited

U.S. PATENT DOCUMENTS 4,032,602   6/1977   Mazour et al. ........................ 260/972

OTHER PUBLICATIONS

Lippman, "Jour. of Organic Chemistry", vol. 30, (1965), pp. 3217–3218.
Cook et al., "Jour. of the Chemical Society", (London), 1949, pp. 2921–2927.

*Primary Examiner*—Anton H. Sutto
*Attorney, Agent, or Firm*—Burgess, Dinklage & Sprung

[57] ABSTRACT

In the production of phosphorous or phosphonous acid ester chlorides of the formula

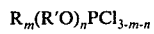

$$R_m(R'O)_nPCl_{3-m-n}$$

wherein
R and R' are various organic radicals,
$m = 0$ or 1,
$n = 1$ or 2, and
$m + n = 1$ or 2, by reacting a trialkylphosphite, a triarylphosphite, a dialkylchlorophosphite or a diarylchlorophosphite with phosphorustrichloride, phosphorous acid alkyl ester dichloride, phosphorous acid aryl ester dichloride, or by reacting a dialkyl-phosphonite with dichlorophosphonite, at a temperature between about $-10°$ C and $120°$ C, the improvement which comprises effecting the reaction in the presence of a catalytic quantity of a compound of at least one of 3– and 5-valent phosphorus, e.g. a phosphine, phosphine oxide, phosphine sulfide, halogen-phosphorane or phosphoric acid-trisamide. A small amount of an alcohol or dialkalphosphite increases the yield.

5 Claims, No Drawings

CATALYZED PRODUCTION OF PHOSPHOROUS AND PHOSPHONOUS ACID ESTER CHLORIDES

The present invention relates to an improved process for the production of phosphorous acid ester chlorides or phosphonous acid ester chlorides of the general formula:

$$R_m(R'O)_n PCl_{3-m-n}$$

wherein
- R represents an alkyl radical containing 1 to 5 C-atoms, which is optionally substituted by halogen or alkoxy groups, or it represents an aryl radical containing up to 8 C-atoms,
- R' represents an alkyl radical containing 1 to 15 C-atoms, optionally substituted by halogen, alkoxy groups or aryl groups, or it represents an aryl radical containing up to 8 C-atoms,
- $m$ represents 0 or 1, and
- $n$ represents 1 or 2, and wherein $m + n = 1$ or 2.

Phosphorous acid ester chlorides and phosphonous acid ester chlorides are important starting materials for organophosphorous plant-protection and flame-proofing agents. By substituting the halogen atoms, phosphorous acid ester dichlorides, for example, react with alcohols and phenols to form phosphorous acid diesters, -diester-halides or -triesters according to reaction conditions. Their reaction with mercaptans gives for example thiophosphorous acid-O,S-diester-halides, while their reaction with primary or secondary amines gives phosphorous acid ester amide-halides or -ester-diameters (cf. Houben-Weyl, Methoden der organ. Chemie, Bd. XII/2, 1964, S. 19, for example).

The corresponding triesters and diesters may be produced from phosphorous acid diester halides by using alcohols or phenols, the diesters by using water, and the thiophosphorous acid-O,O,S-triester by using mercaptans and thiophenols. Primary and secondary amines react to form phosphorous acid diester amides. Furthermore, the free pair of electrons on the phosphorous readily enters into reactions with electrophilic groups. In this way, thiophosphoric acid-O,S-diester-chlorides are formed for example from phosphorous acid-diester-chlorides and sulfenic acid chlorides with elimination of alkyl chloride (cf. Houben-Weyl, Bd. XII/2, 1964, S. 51 and 52, for example). The phosphonous acid ester chlorides enter into similar reactions.

In the past, phosphorous acid ester halides were produced from alcohols or phenols and phosphorus trihalides with elimination of hydrogen halide or by means of a symproportionation from phosphorous acid triesters and -trihalides.

According to the first of the above-mentioned known methods, phosphorus acid-ethyl ester-dichloride for example may be produced in yields of 52% (in diethyl ether as solvent; Saunders et al., J. Chem. Soc. London 1949, 2921) or 40% (without solvent, Schwarz und Geulen, Ber. 90, 952 (1957)). Phosphorous acid-di-ethyl ester-chloride is produced merely in a 36% yield from phosphorus trichloride and ethanol, even in the presence of a tertiary amine in solvents (Houben-Weyl, Bd. XII/2, 1964, S. 46, as well as Saunders, l.c.). The reasons for the poor yield are that the undesired mixed ester chloride is also produced in the reaction mixture. In addition, the hydrogen halide liberated acts by acid cleavage on R—O—P-bonds with the formation of alkyl chloride.

The reaction according to the second of the above-mentioned methods is much less problematical, without the elimination of hydrogen halide and the complications which it involves. However, the difficulty here lies in the slow reaction velocity. For example, since the reaction of phosphoroustrichloride with triethylphosphite at 20° C. produces a yield of about 60% of $C_2H_5OPCl_2$ or $(C_2H_5O)_2PCl$ only after some seven days, an increase in the reaction temperature is required. However, at higher temperatures, the decomposition of the products in the reaction mixture begins with elimination of ethyl chloride and formation of pyrophosphites. The yields of $(C_2H_5O)_2PCl$ obtained, amounting to 44% (Saunders, l.c.; 30 minutes reflux boiling) and 6% (Lippmann, J. Org. Chem. 30, 3217 (1965; 30 minutes 85° C.) were thus unsatisfactory and insufficient for commercial production.

An object of the present invention was thus to provide a method which does not have the said drawbacks.

The present invention therefore provides a method for the production of phosphorous acid ester chlorides or phosphonous acid ester chlorides of the general formula:

$$R_m(R'O)_n PCl_{3-m-n}$$

wherein
- R represents an alkyl radical having 1 to 5 C-atoms, which may optionally be substituted by halogen or alkoxy groups, or it represents an aryl radical having up to 8 C-atoms,
- R' represents an alkyl radical containing 1 to 15 C-atoms, optionally substituted by halogen, alkoxy groups or aryl groups, or it represents an aryl radical containing up to 8 C-atoms,
- $m$ represents 0 or 1, and
- $n$ represents 1 or 2, and wherein $m + n = 1$ or 2, by reacting trialkyl (or -aryl)-phosphite or dialkyl (or -aryl)-chlorophosphite with phosphorustrichloride or phosphorous acid alkyl (or -aryl)ester dichloride or dialkyl (or -aryl)-phosphonite with dichlorophosphonite, optionally in a solvent at temperatures of between −10° C. and 120° C., which is characterized in that the reaction takes place in the presence of catalytic quantities of compounds of 3- and/or 5-valent phosphorous, optionally with the simultaneous presence of catalytic amounts of an alcohol.

In the context of the present invention, catalytically active compounds of 3- and/or 5-valent phosphorus are those which can be represented by the formula $$R''_a PX_b Y_c$$

in which:
- R'' represents identical or different optionally substituted alkyl radicals or alkenyl residues containing 1 to 12 C-atoms, or it optionally represents substituted aryl residues containing 6 to 8 C-atoms,
- X represents hydrogen, OR'', NR''$_2$ (R'' has the above-mentioned meaning) Cl, Br, PR'''$_2$ and PR'''$_2$Y R''' an alkyl radical containing 1 to 4 C-atoms or an aryl radical containing 6 to 8 C-atoms,
- Y represents O or S,
- $a$ represents 0, 1, 2 or 3,
- $b$ represents 0, 1, 2 or 3, and $c$ represents 0 or 1, the sum of $a+b+c$ amounting to 3, 4 or 5.

In the case where X represents OR", H, PR'''$_2$ or PR'''$_2$Y, it is preferred that $a = 2$; $b = 1$; $a+b+c = 3$ or 4; if X represents Cl or Br, it is preferred that $a = 2$ or 3; $b = 1$, 2 or 3 and $a+b+c = 3$, 4 or 5.

It has surprisingly been found that compounds of 3- and/or 5-valent phosphorus accelerate to a considerable extent the exchange of alkoxy groups for halogens, in particular chlorine, in phosphites and phosphonites. In this way, it is possible not only to reduce the duration of the reaction but also to obtain a stronger concentration of the desired product in the reaction mixture. If a further purification is still required, for example by distillation, this is considerably simplified. In addition, the formation of yellowish to red colored, partially smeary, solids is frequently largely prevented.

An addition of small quantities of alcohol and/or dialkylphosphite, preferably with the same alkyl group as the trialkyl- or dialkylchlorophosphite used, often improves the effectiveness of the catalyst; however, alcohols or dialkylphosphites alone do not have catalytic properties. The quantities of these additives, which may optionally be used, amount to approximately 0.1 to 5% by weight, preferably approximately 0.5 to 2.5%, based on the overall reaction mixture.

Starting compounds for the process according to the invention may be the following compounds: phosphorus trichloride, phosphonous acid dichloride or phosphorous acid-alkyl(-aryl)ester-dichloride and trialkyl (-aryl)phosphite, phosphonous acid dialkyl-(aryl)ester or phosphorous acid-dialkyl(-aryl)ester-chloride. In this context, the term "alkyl" is intended to cover the following groups: methyl, ethyl, propyl, butyl, amyl, hexyl, cyclohexyl, octyl, decyl, dodecyl, tetradecyl as well as the corresponding isomers, allyl, butenyl, benzyl, $\beta$-chloroethyl, $\beta$-chloropropyl, $\beta$-chlorobutyl, $\beta$-methoxyethyl, $\beta$-ethoxyethyl, $\beta$-propoxyethyl, $\beta$-butoxyethyl, $\beta$-phenoxyethyl, $\beta$-pentachlorophenoxyethyl, oligo- or polyethyleneglycolyl, oligo- or polypropyleneglycolyl. Phenyl, tolyl, anisyl or chlorophenyl may be present as "aryl" radicals.

Suitable catalysts for the process according to the invention include, for example, trimethyl-, triethyl-, tripropyl-, tributyl-, trihexyl-, tricyclohexyl-, trioctyl-, tridecyl- or tribenzylphosphine, mixed substituted phosphines such as dimethylbutyl-, dimethylphenyl-, dioctylphenyl- or butyldiphenylphosphine, as well as the corresponding isomers, also cyclic phosphines such as 1-phenyl- and 1-methylphospholane, 1-phenyl-3-methyl and 1,3-dimethylphospholine, dimethyl-, diethyl-, dipropyl-, dibutyl-, dihexyl-, dicyclohexyl-, dioctyl- ordi-2-ethylhexyl-phosphine or -halogenphosphine, -alkoxyphosphine, -aroxyphosphine, -dialkylaminophosphine -dialkyl-(diaryl)-phosphino-phosphine, the oxides, sulfides and halogen-phosphoranes derived from the said compounds, also phosphoric acid-tris-amides, e.g. trisalkyl-amides, as well as compounds which are converted into the above-mentioned substances in the reaction mixture, such as the hydrohalides of the phosphine oxides for example.

Substances which are particularly preferred include tributylphosphine, tributylphosphineoxide, tributylphosphinesulfide, tris-2-ethylhexylphosphine or -phosphineoxide or -phosphine-sulfide, tri-n-octyl-phosphine or -phosphineoxide or -phosphine-sulfide, 1-methylphospholane-sulfide, 1-methylphospholine-oxide or — sulfide, as well as phosphoric acid-tris-dimethylamide.

The quantity of the catalyst to be used in accordance with the invention is approximately 0.1 to 5% by weight, based on the sum of the reactants. It has an upper limit, owing to economic considerations only. The use of approximately 0.5 to 2% by weight of catalyst is preferred.

The process according to the invention is for example carried out by simultaneously introducing the calculated amounts of reactants, optionally dissolved in solvents such as halogenated, aliphatic or aromatic hydrocarbons, for example, dichloromethane, 1,2-dichloroethane, cyclohexane, toluene, or ethers, for example diethylether, di-n-butylether, di-i-propylether or tetrahydrofuran, into a reaction vessel with stirring and cooling. The reaction temperature should be maintained between about $-10°$ and $120°$ C., preferably between $0°$ and $80°$ C. The pressure is not critical, but the process is carried out at approximately atmospheric pressure, for the sake of simplicity. Of course, it may take place at any other, in particular elevated pressure. The duration of the reaction depends on the reaction temperature, the catalyst and its concentration. Therefore, it is variable within wide limits.

The reaction may take place discontinuously as well as continuously for example, by collecting the overflow in a residence vessel after mixing the components in a reactor.

In order to purify the desired product, distillation, for example under a vacuum, may follow. The catalyst can usually be easily recovered from the distillation residue; for example, phosphine oxides may be extracted with a solvent such as methylene chloride after treatment with water.

The process according to the invention is described in detail in the following examples.

The yields and compositions mentioned therein are determined by gas chromatography. The data are given in percent per unit area. 2-Ethylhexyl is understood by i-$C_8H_{17}$. All examples were carried out under nitrogen in the absence of moisture. $PCl_3$ and triethylphosphite were used in the form of commercial products; triethylphosphite contains about 1 to 2.5% diethylphosphite and about 0.2 to 1% ethanol according to the gas chromatogram.

COMPARATIVE EXAMPLE 137.5 g (1 mol) of phosphorustrichloride and 83 g (0.5 mol) of triethylphosphite were simultaneously added dropwise into a flask within 30 minutes and mixed together by stirring while cooling at $20°-24°$ C. The mixture was subsequently left to stand at $20°$ C., then at $30°$ C., and the composition of the solution was determined.

| composition | $PCl_3$ | $C_2H_5OPCl_2$ | $(C_2H_5O)_2PCl$ |
| --- | --- | --- | --- |
| at the end of the mixing process: | 28% | 32% | 36% |
| after a further 85 h at $20°$ C: | 18% | 35% | 23% |
| after a further 72 h at $35°$ C: | 17% | 58% | 20% |

EXAMPLE 1

2 g of (n-$C_8H_{17}$)$_3$PO were dissolved in triethylphosphite in an experiment carried out in the same manner as in the comparative example.

| composition | PCl₃ | C₂H₅OPCl₂ | (C₂H₅O)₂PCl |
|---|---|---|---|
| at the end of the mixing process: | 23% | 44% | 31% |
| after a further 72 h at 20° C: | 2% | 95% | 2% |

EXAMPLE 2

68.7 g (0.5 mol) of phosphorustrichloride and 166 g (1 mol) of triethylphosphite, in which 2 grams of tris-2-ethylhexyl-phosphineoxide were dissolved, were simultaneously added dropwise into a flask within 30 minutes and mixed together by stirring while cooling at 48° to 52° C. At the end of the mixing process, the colorless slightly cloudy solution had the following composition: 6% C₂H₅OPCl₂; 85% (C₂H₅O)₂PCl; 5% (C₂H₅O)₃P. In order to obtain pure phosphorous acid-diethyl esterchloride, the high boiling constituents were first separated off at 10mm Hg and at a head temperature of 38° to 50° C. in a rapid distillation and the distillate was subsequently subjected to fine distillation. The product obtained at 33mm Hg and a head temperature of 60° to 62° C. was of 96% priority and its H-NMR agreed with the expected structure.

EXAMPLES 3–9 (see Table 1)

An analogous process to Example 1 was followed. The catalyst was dissolved in phosphorustrichloride in Examples 4 and 8 and in triethylphosphite in Examples 3, 5 to 7 and 9.

EXAMPLES 10–17 (see Table 2)

The process was carried out in analogous manner to Example 2. The catalyst was in each case dissolved in triethylphosphite.

EXAMPLES 18–26 (see Tables 3 and 4)

Whereas Examples 18 and 25 were carried out analogously to Example 1, the trialkyl(-aryl)phosphite, which contained the dissolved catalyst, was initially introduced in Examples 20 to 23 and the phosphorustrichloride was added dropwise with stirring and cooling.

Table 1

| No. | Catalyst | Reaction temperature | After-reaction | Composition of the mixture formed | | | Description of the mixture |
|---|---|---|---|---|---|---|---|
| | | | | PCl₃ | C₂H₅OPCl₂ | (C₂H₅O)₂PCl | |
| 3 |  | 20° C | 66 h at 20° C | 9% | 77% | 11% | yellow, very little solid matter |
| 4 | 2 g (C₄H₉)₃P | 23° C | 24 h at 20° C | 6% | 87% | 4% | dark yellow, some solid |
| 5 | 2 g (C₄H₉)₃PO | 50° C | 92 h at 20° C | 3% | 93% | 2% | yellow, slightly cloudy |
| 6 | 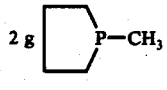 | 23° C | 60 h at 20° C | 4% | 88% | 5% | orange, some solid |
| 7 | 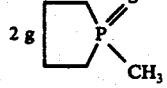 | 22° C | 24 h at 22° C | 12% | 71% | 14% | colorless clear |
| 8 |  | 20° C | 24 h at 23° C | 15% | 66% | 15% | yellow slightly cloudy |
| 9 | 4 g C₆H₅P(C₄H₉)₂ | 22° C | — | 13% | 69% | 16% | yellow, some solid |

Table 2

| No. | Catalyst | Reaction temperature | After reaction | Composition | | | Description of the mixture |
|---|---|---|---|---|---|---|---|
| | | | | C₂H₅OPCl₂ | (C₂H₅O)₂PCl | (C₂H₅O)₃P | |
| 10 | 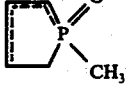 | 8° C | 5 h at 16° C | 10% | 67% | 17% | yellowish, some yellowish solid |
| 11 | 2g (C₄H₉)₃PS | 40° C | ½ h at 40° C | 18% | 51% | 24% | colorless, clear |
| 12 | 2g (i-C₈H₁₇)₃PS | 40° C | ½ h at 40° C | 21% | 45% | 27% | colorless, clear |
| 13 | 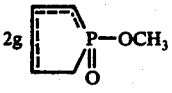 | 40° C | — | 21% | 44% | 29% | colorless, clear |

Table 2-continued

| No. | Catalyst | Reaction temperature | After reaction | Composition C₂H₅OPCl₂ | (C₂H₅O)₂PCl | (C₂H₅O)₃P | Description of the mixture |
|---|---|---|---|---|---|---|---|
| 14 | 2g (CH₃)₂P—H ‖ O | 40° C | — | 15% | 58% | 18% | slightly yellowish cloudy |
| 15 | 2g (i-C₈H₁₇)₂P—H ‖ O | 40° C | — | 20% | 46% | 28% | colorless, clear |
| 16 | 2g [(CH₃)₂P ‖ S]₂ | 40° C | — | 19% | 49% | 26% | colorless, clear |
| 17 | 2g [(CH₃)₂N]₃PO | 50° C | — | 2% | 87% | 3% | colorless, cloudy |

Table 3

PCl₃ + ½ (RO)₃P → 1½ (RO)PCl₂

| No. | R | Quantity of catalyst per mol of PCl₃ | Reaction temperature | After-reaction | Composition of the mixture produced PCl₃ | (RO)PCl₂ | (RO)₂PCl | Description |
|---|---|---|---|---|---|---|---|---|
| 18 | CH₃ | 0.5 g (i-C₈H₁₇)₃PO | 24° C | 70 h at 22° C | 14% | 69% | 12% | slightly yellow, cloudy |
| 19 | CH₃ | nil | 24° C | 170 h at 22° C | 28% | 45% | 23% | yellow, cloudy |
| 20 | n-C₆H₁₃ | 1g (i-C₈H₁₇)₃PO | 40° C | 20 h at 40° C | 7% | 75% | 12% | colorless, clear |
| 21 | n-C₁₀H₂₁ | 1g (i-C₈H₁₇)₃PO | 80° C | 250 h at 21° C | 14% | 82% | unidentified | colorless, clear |

Table 4

Reaction ½ PCl₃ + (RO)₃P → 1½ (RO)₂PCl

| No. | R | Quantity of catalyst per mol of (RO)₃P | Reaction temperature | After-reaction | Composition of the mixture produced ROPCl₂ | (RO)₂PCl | (RO)₃P | Description |
|---|---|---|---|---|---|---|---|---|
| 22 | n-C₄H₉-O-CH₂-CH₂ | 1g (i-C₈H₁₇)₃PO | 40° C | — | 10% | 67% | 13% | colorless, clear |
| 23 | C₆H₅ | 2g (i-C₈H₁₇)₃PO | 70° C | 3 h 70° C | 6% | 53% | 41% | colorless, clear |
| 24 | C₆H₅ | nil | 70° C | 3 h 70° C | — | 4% | 84% | colorless, clear |
| 25 | Cl-CH₂-CH₂⁺ | 2g (i-C₈H₁₇)₃PO | 40° C | — | 9% | 70% | 7% | colorless, clear |
| 26 | Cl-CH₂-CH₂⁺ | nil | 40° C | — | 19% | 39% | 28% | colorless, clear |

EXAMPLE 27

332 g (2 mol) of triethylphosphite, in which 4.7 g of dibutyl-diethylamino-phosphine oxide were dissolved, and 137.5 g of phosphoroustrichloride (1 mol), which was dissolved in 250 ml dichloromethane, were simultaneously added dropwise to a flask over a period of 1 hour and mixed by stirring. The mixture was cooled by boiling dichloromethane. The mixture formed had the following composition: 46% of dichloromethane; 7% C₂H₅OPCl₂; 32% (C₂H₅O)₂PCl; 9% (C₂H₅O)₃P.

EXAMPLE 28

17.5 g (0.15 mol) of methyldichlorophosphine were added dropwise to 20.4 g (0.15 mol) of methanephosphonic acid-diethylester (91%) and 0.8 g of tris-2-ethylhexylphosphine oxide with cooling over 20 minutes at 20° C. The mixture formed contained 53% of methanephosphonic acid-ethylester-chloride.

EXAMPLE 29

73.5 g (0.5 mol) of ethyldichlorophosphite, in which 0.8 g of tributylphosphine were dissolved, and 83 g (0.5 mol) of triethylphosphite were simultaneously added dropwise to a flask over a period of 30 minutes and mixed by stirring with cooling at 30° C. The mixture produced contained 71% of (C₂H₅O)₂PCl.

EXAMPLE 30 (see Table 5)

In 3 comparative experiments, triethylphosphite having different ethanol and diethylphosphite contents was reacted with PCl₃ in the strict absence of moisture. The reaction conditions and quantities used in this example correspond to the data given in Example 2.

Table 5

| No. | Triethylphosphite content of C₂H₅OH | (C₂H₅O)₂POH | Composition of the mixture formed C₂H₅OPCl₂ | (C₂H₅)₂PCl | (C₂H₅O)₃P | Description of the mixture |
|---|---|---|---|---|---|---|
| 30a | 0.2% | 1.1% | 15% | 57% | 22% | colorless, slightly cloudy |

Table 5-continued

| No. | Triethylphosphite content of $C_2H_5OH$ | $(C_2H_5O)_2POH$ | Composition of the mixture formed $C_2H_5OPCl_2$ | $(C_2H_5)_2PCl$ | $(C_2H_5O)_3P$ | Description of the mixture |
|---|---|---|---|---|---|---|
| 30b | 0.2% | 2.6% | 12% | 70% | 14% | colorless, slightly cloudy |
| 30c | 0.8% | 1.1% | 3% | 86% | 5% | colorless, slightly cloudy |

It will be appreciated that the instant specification and examples are set forth by way of illustration and not limitation, and that various modifications and changes may be made without departing from the spirit and scope of the present invention.

What is claimed is:

1. In the production of phosphorous acid ester chlorides or phosphonous acid ester chlorides of the formula $$R_m(R'O)_nPCl_{3-m-n}$$

wherein
R represents an alkyl radical containing 1 to 5 C-atoms, which may optionally be substituted by halogen or alkoxy groups, or it represents an aryl radical having up to 8 C-atoms,
R' represents an alkyl radical having 1 to 15 C-atoms, optionally substituted by halogen, alkoxy groups or aryl groups, or it represents an optionally substituted aryl radical containing up to 8 C-atoms,
$m$ represents 0 or 1, and
$n$ represents 1 or 2, and wherein $m + n = 1$ or 2,
by reacting a trialkylphosphite, a triarylphosphite, a dialkylchlorophosphite or a diarylchlorophosphite with phosphorustrichloride, phosphorus acid alkyl ester dichloride, phosphorous acid aryl ester dichloride, dialkylphosphonite plus dichloro-phosphonite or diarylphosphonite plus dichlorophosphonite at a temperature between about −10° C. and 120° C., the improvement which comprises effecting the reaction in the presence of a catalytic quantity of at least one compound selected from the group consisting of a phosphine, a phosphine oxide, a phosphine sulfide, a halogen-phosphorane, phosphoric acid-tris-amide and a phosphoric acid-tris-alkyl-amide.

2. A process according to claim 1, wherein the catalyst is present in about 0.1 to 5% by weight of the reaction mixture.

3. A process according to claim 1, wherein the reactants contain alkyl radicals and the reaction is also effected in the presence of about 0.1 to 5% by weight of the reaction mixture of an alkanol, dialkyl-phosphite or mixtures thereof having the same alkyl radical as the reactants.

4. A process according to claim 1, wherein the catalyst comprises phosphoric acid-tris-dimethylamide.

5. A process according to claim 4, wherein the catalyst is present in about 0.5 to 2% by weight of the reaction mixture, the reactants contain alkyl radicals and the reaction is effected in the presence of about 0.5 to 2.5% by weight of the reaction mixture of an alkanol, dialkyl-phosphite or mixtures thereof having the same alkyl radical as the reactants.

* * * * *

UNITED STATES PATENT AND TRADEMARK OFFICE
CERTIFICATE OF CORRECTION

PATENT NO. : 4,118,435
DATED : October 3, 1978
INVENTOR(S) : Roland Kleinstück et al It is certified that error appears in the above-identified patent and that said Letters Patent are hereby corrected as shown below:

Column 1, lines 33-34  "-diameters" should be --diamides--

Columns 7,8  Table 4, footnote  insert --+ the $(Cl-CH_2-CH_2-O)_3P$ used was only 88% pure--

Signed and Sealed this

Fourth Day of December 1979

[SEAL]

Attest:

SIDNEY A. DIAMOND

*Attesting Officer*　　*Commissioner of Patents and Trademarks*